United States Patent
Brickwood

(10) Patent No.: US 7,179,641 B2
(45) Date of Patent: *Feb. 20, 2007

(54) DEVICE FOR MOTILE SPERM SEPARATION

(75) Inventor: David Brickwood, Kingston-Upon-Thames (GB)

(73) Assignee: Genosis (UK) Limited, Surrey (GB)

( * ) Notice: Subject to any disclaimer, the term of this patent is extended or adjusted under 35 U.S.C. 154(b) by 606 days.

This patent is subject to a terminal disclaimer.

(21) Appl. No.: 10/203,318

(22) PCT Filed: Feb. 16, 2001

(86) PCT No.: PCT/GB01/00654

§ 371 (c)(1),
(2), (4) Date: Oct. 16, 2002

(87) PCT Pub. No.: WO01/60968

PCT Pub. Date: Aug. 23, 2001

(65) Prior Publication Data

US 2003/0096395 A1    May 22, 2003

(30) Foreign Application Priority Data

Feb. 16, 2000    (GB)    .................................. 0003596.4

(51) Int. Cl.
*C12M 1/34*    (2006.01)
(52) U.S. Cl. .................... 435/288.2; 435/287.2; 435/287.7; 435/287.9
(58) Field of Classification Search ............ 435/287.7, 435/287.9, 288.2
See application file for complete search history.

(56) References Cited

U.S. PATENT DOCUMENTS

| | | |
|---|---|---|
| 5,866,354 A | 2/1999 | Froman |
| 5,908,380 A | 6/1999 | Zavmaboupes-Zavos |
| 6,391,654 B1 * | 5/2002 | Bateman ..................... 436/518 |

FOREIGN PATENT DOCUMENTS

| | | |
|---|---|---|
| FR | 2 539 628 | 7/1984 |
| WO | WO 9966331 A1 * | 12/1999 |

OTHER PUBLICATIONS

Database WPI, Section PQ, Week 199013, Derwent Publications Ltd., London, GB; AN 1990-097584 XP00215576 & SU 1 486 163 A (Kuban Agric Inst), Jun. 15, 1989.

* cited by examiner

*Primary Examiner*—William H. Beisner
(74) *Attorney, Agent, or Firm*—Wenderoth, Lind & Ponack, L.L.P.

(57) ABSTRACT

An apparatus for separating and detecting motile spermatozoa in a liquid sample, comprises: a separation vessel including (i) an inlet port, (ii) an outlet port arranged to be opened, (iii) a separation medium into which motile spermatozoa in the sample can flow via the inlet port, and (iv) an actuator operable to open the outlet port for allowing the separation medium to flow out of the vessel through the outlet port; and a spermatozoa detection device including (i) an application zone in communication with the outlet port, (ii) a detection zone, in which presence of spermatozoa can be detected, and (iii) a reagent zone containing a reagent which is capable of reacting with spermatozoa to facilitate detection of the spermatozoa in the detection zone, with the application zone, the detection zone and the reagent zone being arranged to permit capillary flow of spermatozoa from the application zone to the detection zone.

28 Claims, 14 Drawing Sheets

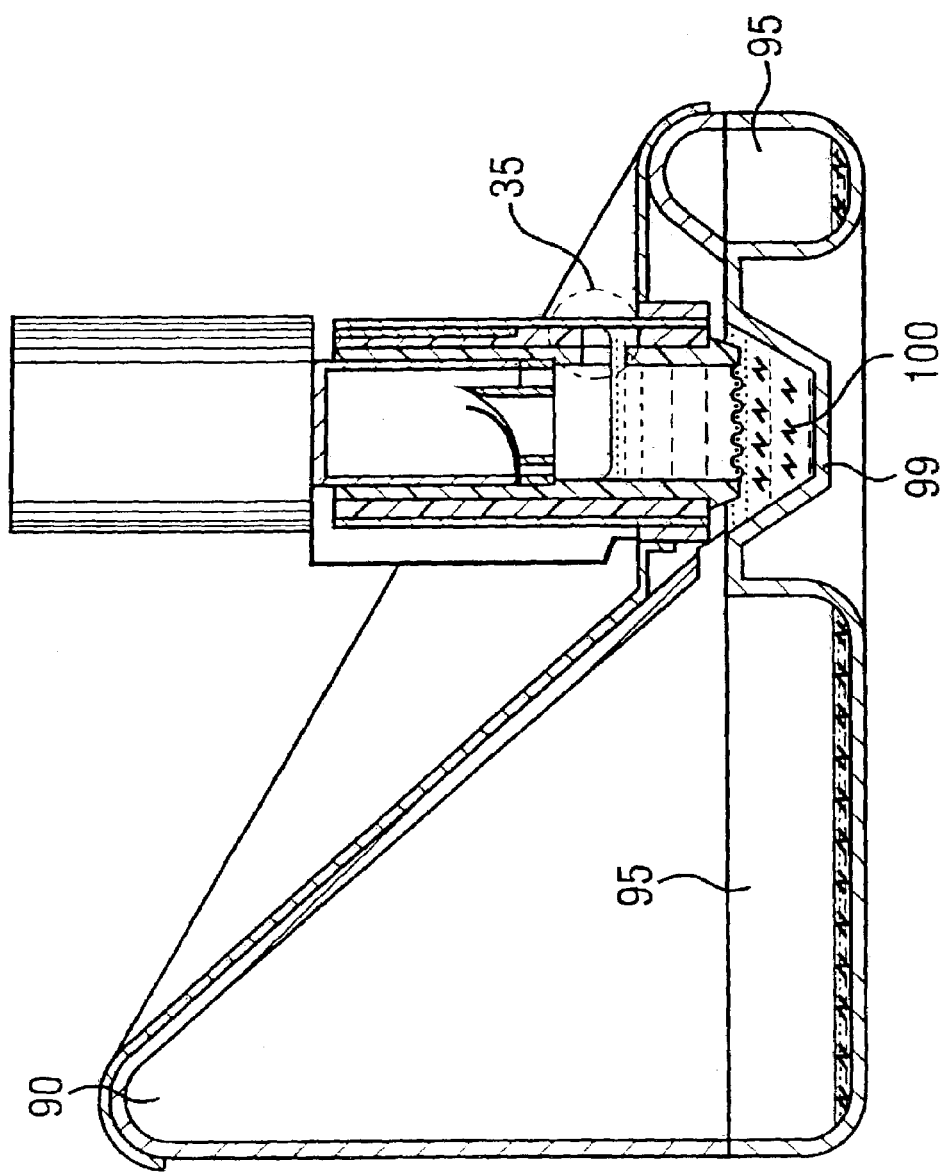

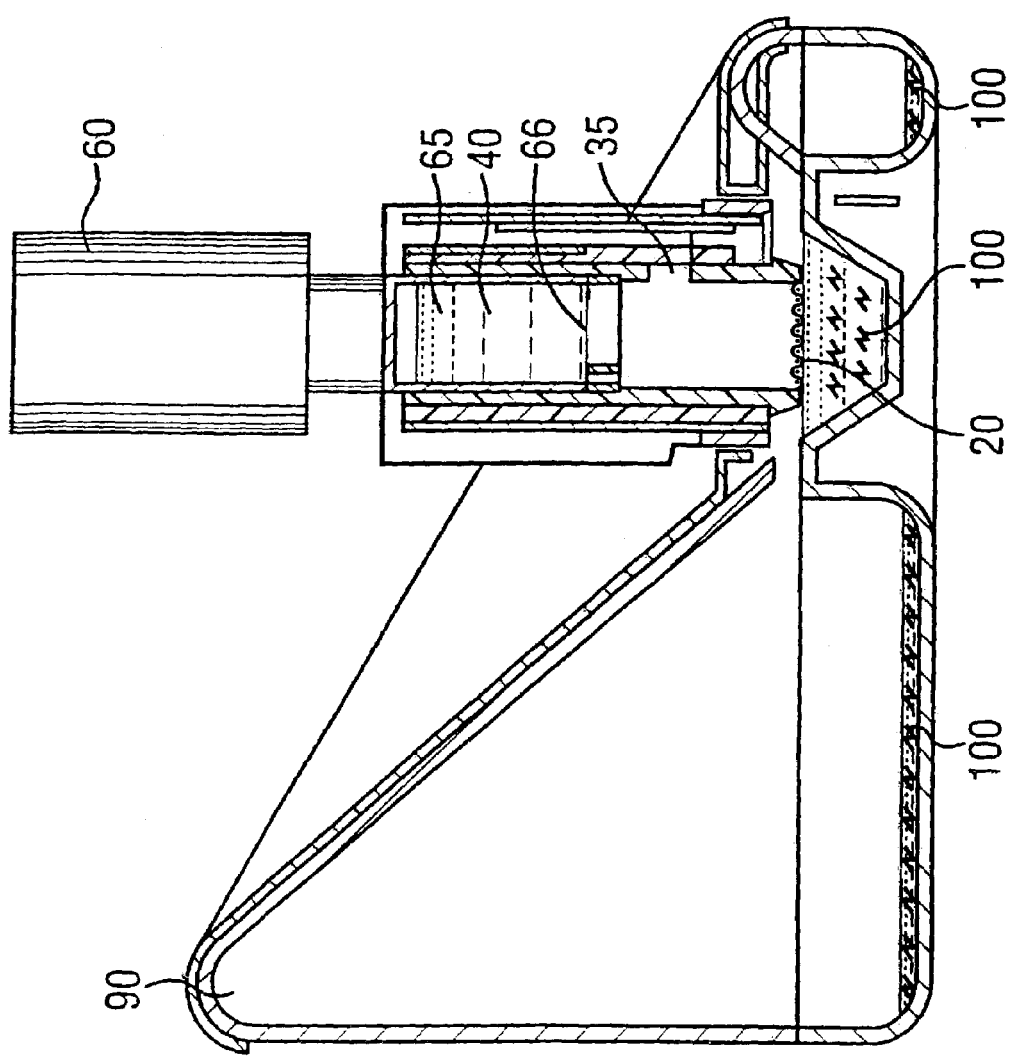

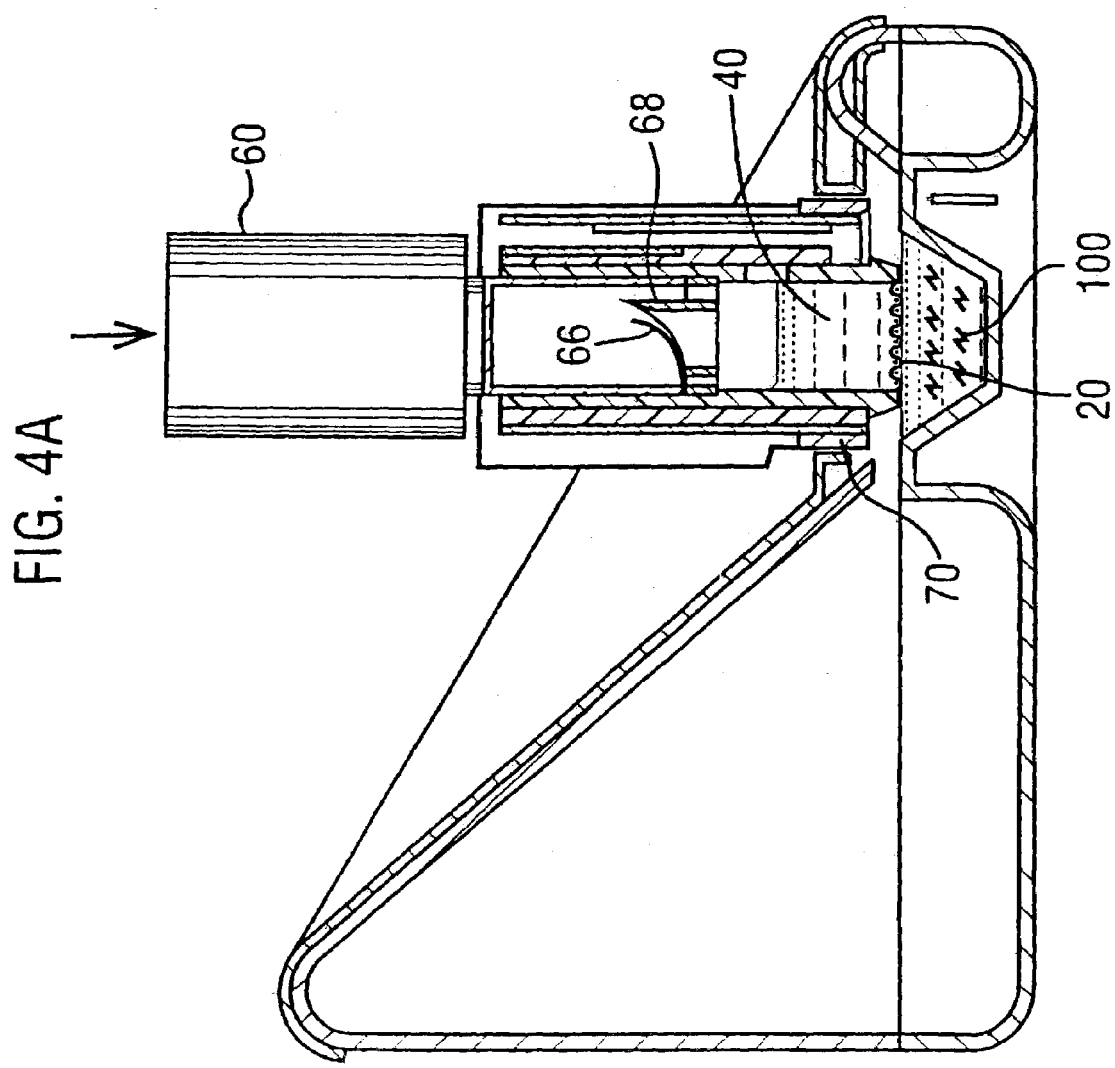

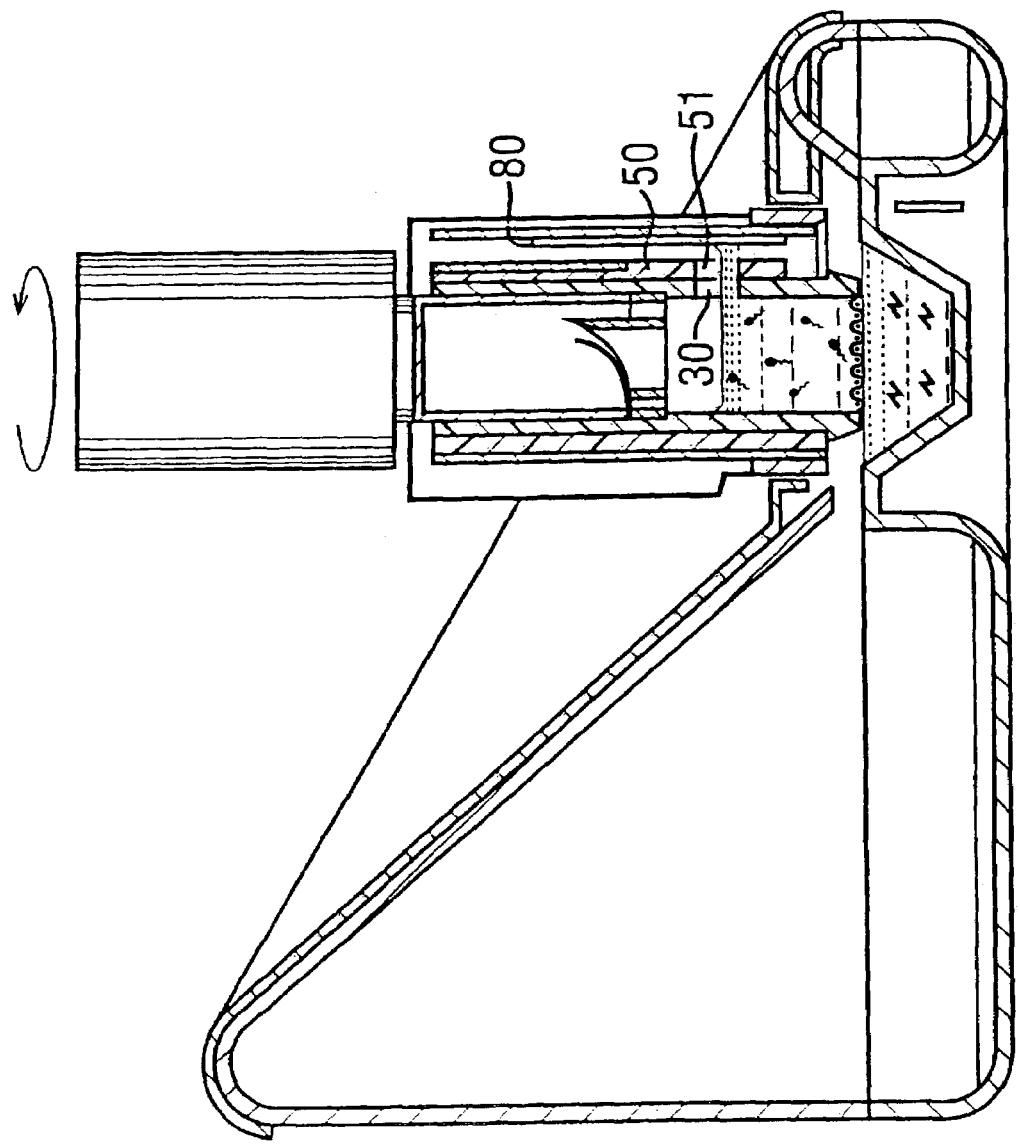

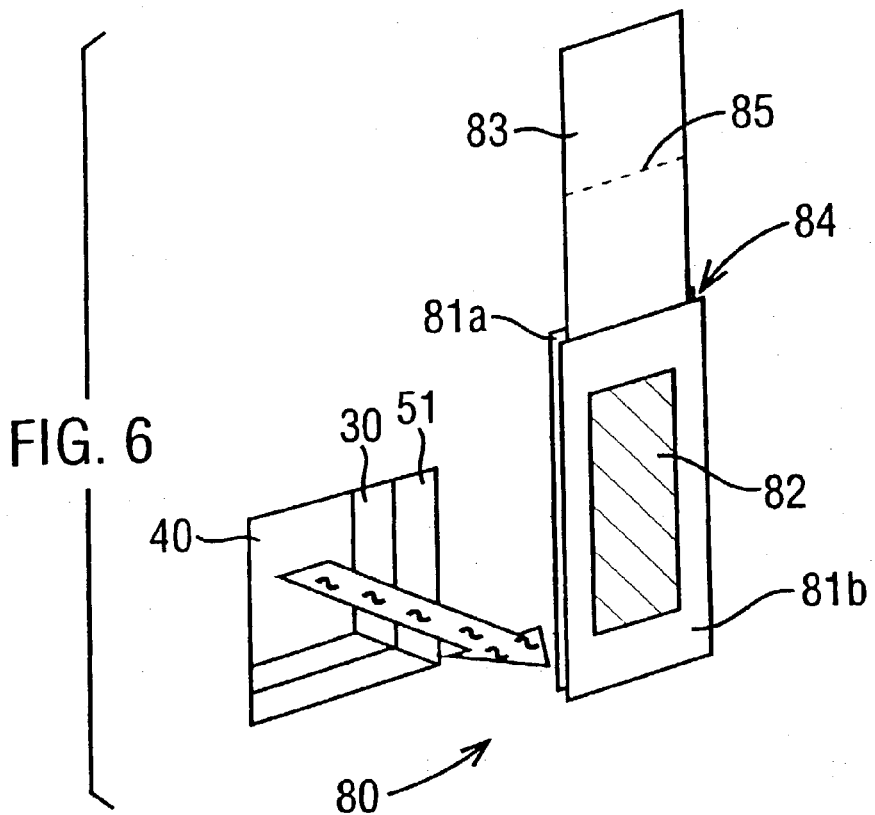
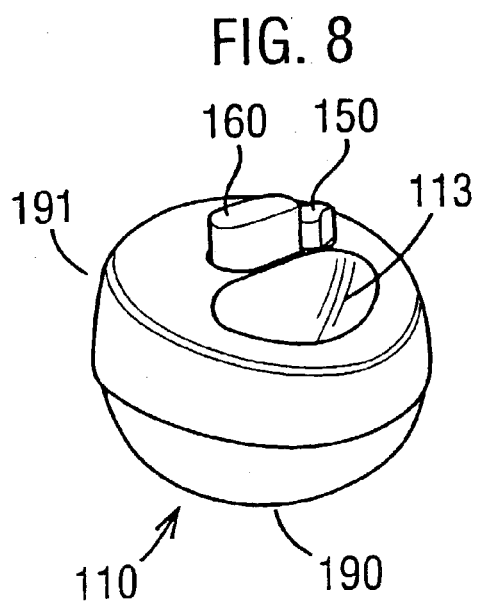
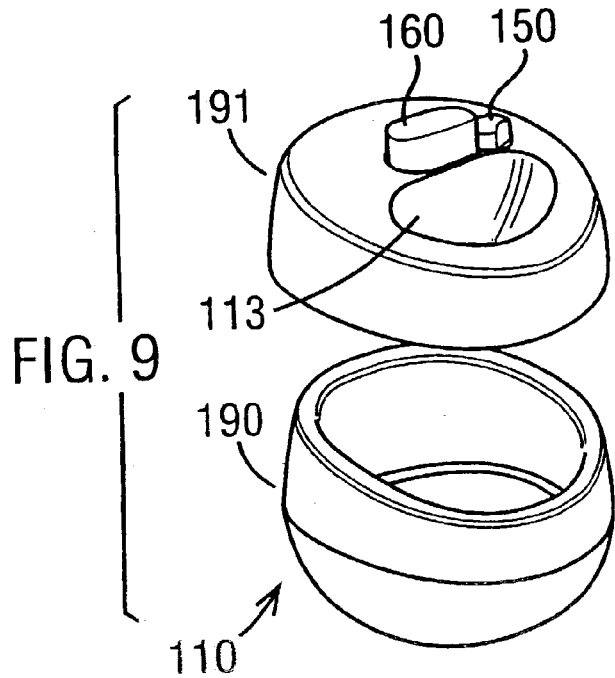

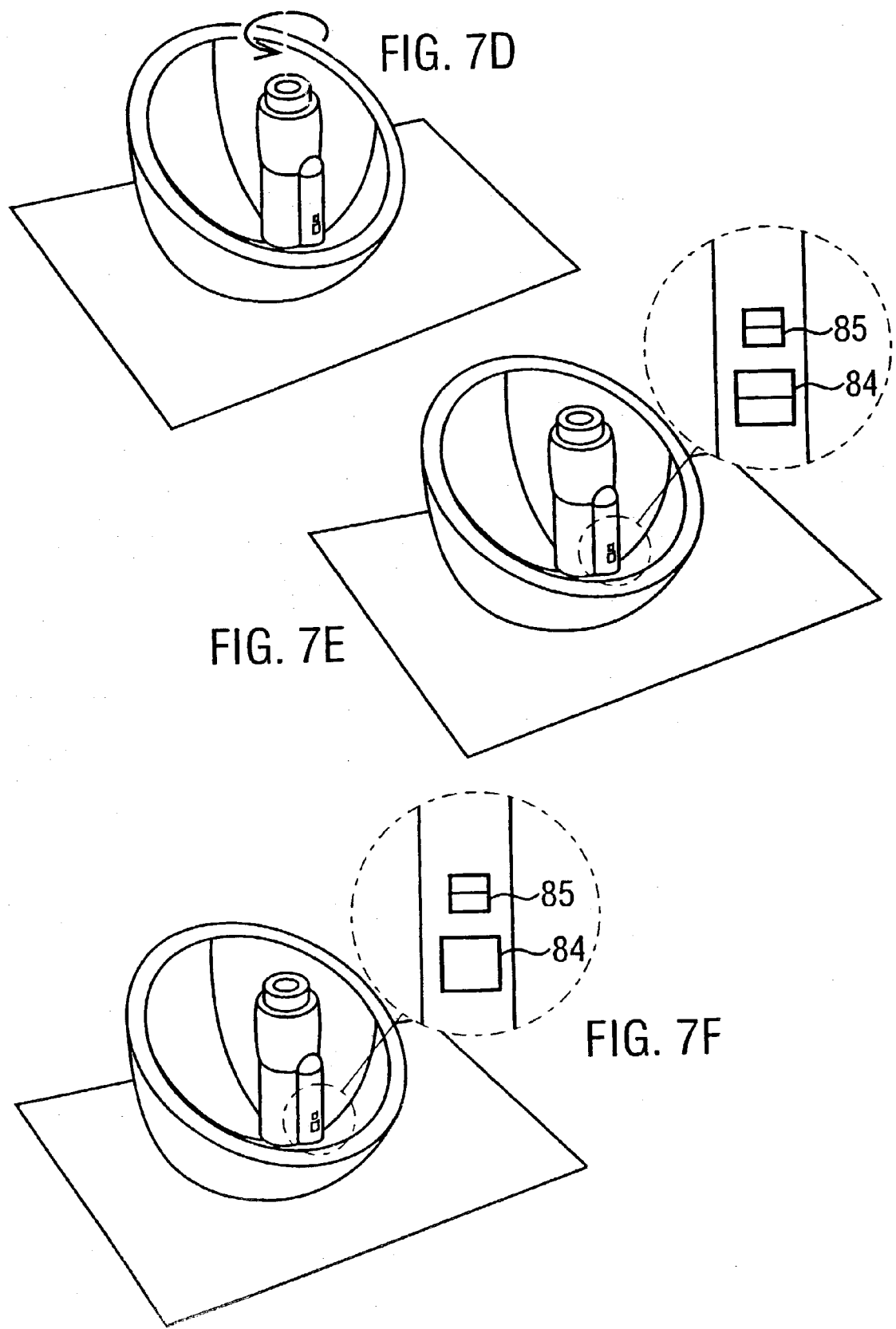

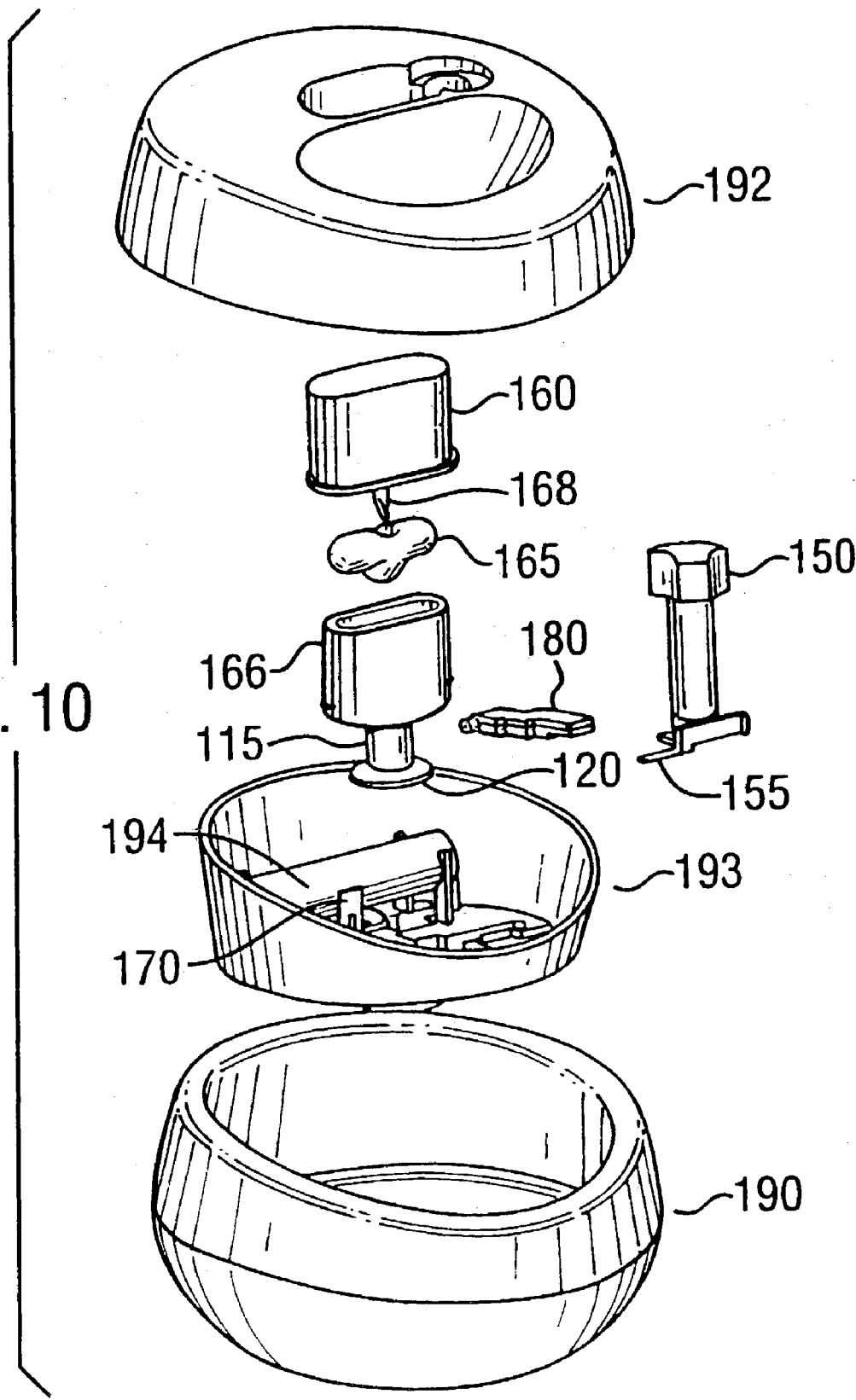

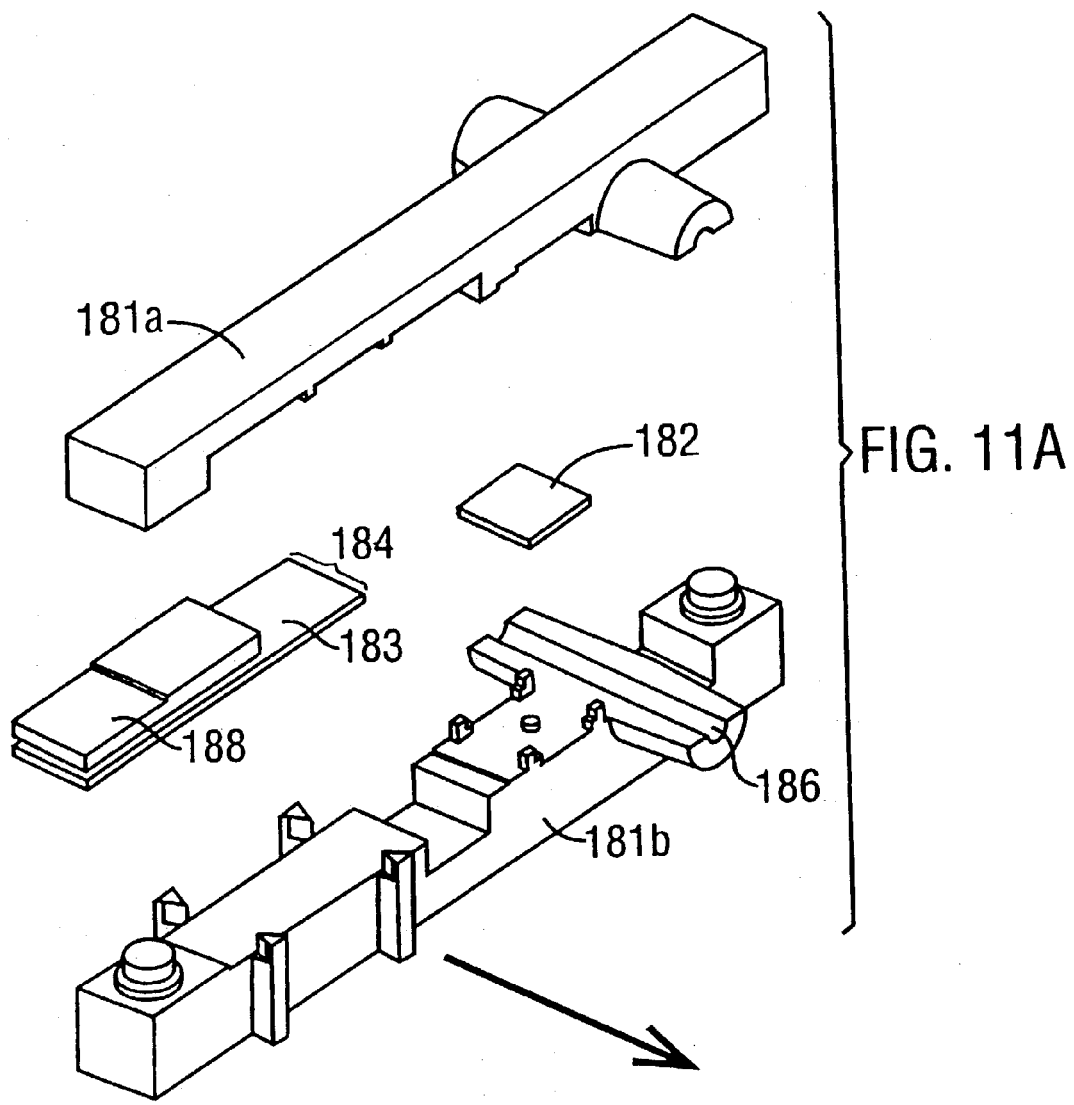
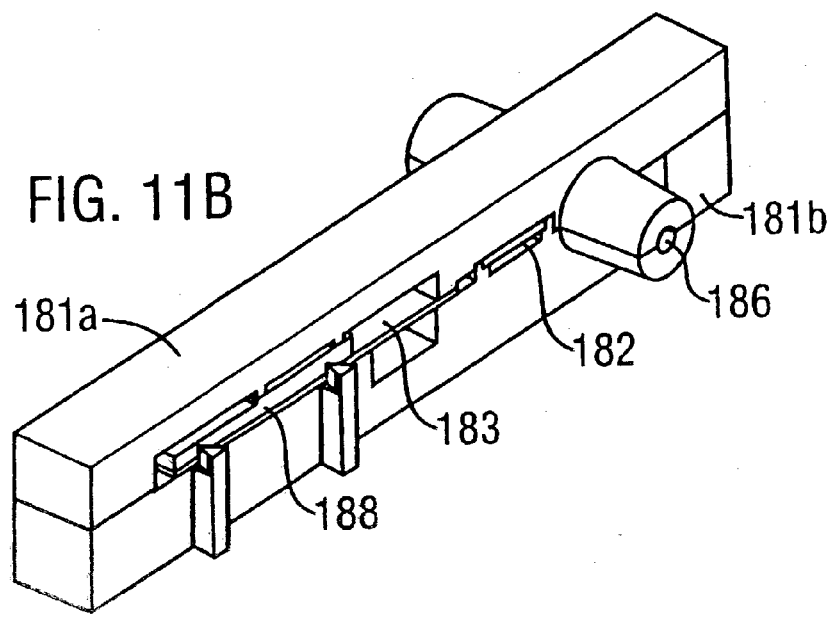

DEVICE FOR MOTILE SPERM SEPARATION

All documents cited herein are incorporated by reference in their entirety.

TECHNICAL FIELD

This invention is in the field of male fertility tests, more specifically tests for separating and detecting motile spermatozoa in a semen sample.

BACKGROUND ART

Approximately 15% of couples attempting to conceive fail to do so within one year of unprotected intercourse. Fertility specialists define these couples as being infertile. 40% of these cases result from male factors. In a substantial proportion of these, treatment is available to ameliorate or relieve a condition which leads to infertility.

Other conditions also exist in which it is desirable to test for presence or otherwise of viable spermatozoa in a sample. For example, vasectomies are now frequently performed as a method of contraception, but it is necessary to confirm that ejaculate is free of viable spermatozoa after this operation.

A number of methods exist for assessing motility and number of spermatozoa in a sample. One such method is microscopic analysis, which is typically performed in a hospital or commercial laboratory. More recently, however, a number of proposals have been made for test kits which are intended to simplify detection of spermatozoa.

W097/40386 discloses a kit which is based on immunodetection of the 34 kDa human epididymal spermatozoa protein. Spermatozoa in a sample are washed three times by centrifugation in Dulbecco-phosphate buffered saline. These samples are then heat denatured at 95° C., centrifuged at 14000 g, and supernatants are then used for analysis.

W095/29188 describes a test based on antibodies applied to the SP-10 antigen of human spermatozoa.

EP-A-0387873 discloses a kit which uses solid beads to which are bound antibody specific to the human spermatozoon acrosome. The beads are mixed with a sample, incubated, separated and washed, and a number of spermatozoa bound to the beads is measured, preferably by examination with aid of a microscope.

A disadvantage of these test kits is that they do not distinguish between motile and non-motile spermatozoa. This distinction is a most predictive indicator of male infertility. Moreover, they involve procedures which do not lend themselves to home use (e.g. centrifugation, microscopy), thus requiring implementation by a skilled practitioner.

These disadvantages are addressed by the device of W000/09648 (Genosis Limited), which discloses an apparatus for separating motile spermatozoa from non-motile spermatozoa in a liquid sample, the apparatus comprising: (i) a vessel having a sample receiving inlet, a filtered sample outlet and a sample separation filter mounted therebetween, with the sample separation filter having a sample-receiving surface and an opposed surface, and the sample separation filter being effective substantially to prevent flow of a sample therethrough, but permitting passage of motile spermatozoa therethrough when the opposed surface of the sample separation filter is placed in contact with a liquid medium; and (ii) means for supplying a liquid to the opposed surface of the filter.

Further improvements in sperm separation, detection and analysis are disclosed herein.

SUMMARY OF THE INVENTION

The present invention provides a device for separating motile spermatozoa from a liquid sample, with the device having a sample separation vessel comprising:
  (a) a sample inlet port;
  (b) a sample outlet port, which is initially closed;
  (c) a sample separation medium into which motile spermatozoa in a sample can migrate via the sample inlet port; and
  (d) an actuator operable to open the sample outlet port, thereby allowing the sample separation medium to flow out of the vessel through the sample outlet port.

In this device, the separation medium in the vessel is initially prevented from flowing through the outlet port. This allows an incubation period which allows motile sperm sufficient time to migrate from the sample into the sample separation medium before it exits the vessel. On operation of the actuator, the outlet port is opened and the separation medium (including motile spermatozoa) can migrate through the outlet port and leave the vessel e.g. for analysis.

In order for motile spermatozoa in the sample to enter the separation medium, the inlet port and the separation medium must be in liquid communication. Preferably, however, such communication is initially prevented, thus preventing contamination of the medium via the inlet port before the device is used. This may also prevent the medium from escaping from the vessel via the inlet port, although this may be achieved anyway due to, for instance, viscosity or surface tension of the medium.

In this embodiment, therefore, the vessel comprises (e) a second actuator, operable to bring the separation medium into communication with a sample via the inlet port. This might be achieved by storing the medium remotely from the inlet port until the second actuator is operated or, alternatively, by having an inlet port which is initially closed or sealed, which is opened using the actuator.

During use of this device, therefore, the second actuator is operated, thereby bringing the separation medium and the inlet port into communication. This allows motile spermatozoa in the sample to migrate from the sample into the separation medium. After a period of incubation, the first actuator is operated, thereby allowing the separation medium (now containing motile spermatozoa) to leave the vessel. It is preferred that the first actuator cannot be operated until the second actuator has been operated.

It will he appreciated that feature (e) can operate independently from feature (d).

The vessel may be of circular cross-section e.g. conical or cylindrical.

The inlet and outlet ports can take a variety of forms. For instance, the inlet port might be an open end of a cylinder or cone. This open end can be placed in a sample and, when the separation medium and the sample are in communication, spermatozoa can enter the vessel via the open end. It may he desirable to cover the open end by a mesh or grid, to assist in retaining sample separation medium within the vessel (via surface tension) without preventing entry of spermatozoa from the sample.

The outlet port is preferably an opening, hole or aperture in a wall of the vessel, which may continue into a pipe, tube or conduit leading away from the vessel.

The inlet and outlet ports are preferably arranged such that, during use, the outlet port is above the inlet port.

Spermatozoa thus have to swim against gravity in order to exit the vessel, thereby enhancing a preferential migration of motile vs. non-motile sperm.

Any suitable actuators can be used in the device e.g. buttons, switches and the like. Where the vessel is of circular cross-section, the first actuator is preferably a rotatable collar containing an opening. Rotation of the collar from a closed position aligns openings in the collar and vessel wall, thereby allowing sample separation medium to leave the vessel via the outlet port.

Another preferred form of the first actuator acts to withdraw fluid into a barrel or tube e.g. it withdraws a plunger of a syringe. The plunger will initially block the outlet port but, on withdrawal of the plunger, sample separation medium can flow through the outlet port and into an internal space of the syringe. A suitable actuator for effecting withdrawal of the syringe plunger is a rotatable knob which is attached to the plunger e.g. by a rack and pinion mechanism.

Where the device includes a second actuator, this is preferably a button. When pressed, sample separation medium stored within the device is released so that it reaches (e.g. by gravity) the inlet port. This can be achieved by, for instance, including a reservoir of medium within the vessel, sealed by a foil wall, together with a foil cutter. Operation of the second actuator causes the cutter to pierce the foil, releasing the medium.

A preferred arrangement of the reservoir is that disclosed in United Kingdom patent application 0021665.5, in which the separation medium is held within a hermetically sealed reservoir. The device will include a venting needle for venting the medium from the reservoir, with the venting needle comprising a fluid delivery portion and a reservoir-venting portion, with the reservoir-venting portion being distal along the needle of the delivery portion, and with the delivery portion and the venting portion each defining a channel extending from a respective portion through a sidewall of the needle. The channels allow the delivery portion, in use, to deliver fluid from the reservoir, for example by venting air at one end and dispensing fluid at another. In this arrangement, the venting needle will preferably be at least partially a cannula having a cannulated point at the delivery portion for controlled, pipette-like delivery. In a needle with a proximal portion and a distal portion, the distal portion may comprise both the venting portion and the delivery portion. The needle preferably has a C-shaped section at the venting portion and the delivery portion. The two channels are preferably unitary, with each channel extending from the venting portion to the delivery portion.

In a venting position, the venting needle preferably extends through two wall portions of the reservoir such that the venting portion forms a passage through a first of these wall portions to allow the container to be vented with air, and the delivery portion forms a passage through a second of these wall portions to allow fluid to be dispensed from the reservoir.

Using this sort of arrangement, the needle is operated by the second actuator (e.g. it is attached to a button or a screw-advance mechanism).

The separation medium allows motile spermatozoa, in preference to non-motile sperm, to migrate therethrough. This can be achieved using any suitable buffer (e.g. HEPES, EBSS and the like), as motile spermatozoa will be able to migrate through the medium actively whereas, over a relevant time-scale, non-motile spermatozoa will at best enter passively by diffusion. It is preferred, however, to use a medium that enhances migration of motile spermatozoa from the sample. Suitable media include cervical mucus [e.g. Keel & Webster (1988) *Fertil. Steril.* 49:138–143], polyacrylamide gel [e.g. Lorton et al. (1981) *Fertil. Steril.* 35:222–225], hyaluronic acid [e.g. Aitken et al. (1992) *J. Androl.* 13:44–54], or a cellulose derivative [e.g. international patent application PCT/GB00/03130 (Genosis Limited)] such as methylcellulose.

The medium may be in the form of a solution or a gel.

Advantageously, the separation medium also serves to 'wash' the sample, in order to remove components such as seminal plasma.

In addition to separating motile and non-motile spermatozoa, it is preferred that the device can detect motile spermatozoa after separation. Accordingly, the device of the invention preferably comprises spermatozoa detection means in communication with the vessel outlet port. The detection means may be integral with the device, or may be provided as a separate component for inserting into the device before, during or after sample separation.

Accordingly, the invention provides a device for separating and detecting motile spermatozoa in a liquid sample, with the device having:
  a sample separation vessel comprising:
    (a) a sample inlet port;
    (b) a sample outlet port, which is initially closed;
    (c) a sample separation medium into which motile spermatozoa in a sample can migrate via the sample inlet port; and
    (d) an actuator operable to open the sample outlet port, thereby allowing the sample separation medium to flow out of the vessel through the sample outlet port, and
  spermatozoa detection means comprising:
    (i) an application zone in communication with the outlet port;
    (ii) a detection zone, in which presence of spermatozoa can be detected; and
    (iii) a reagent zone containing a reagent which is capable of reacting with spermatozoa to facilitate their detection in the detection zone,
  with these zones being arranged to permit capillary flow of spermatozoa from the application zone to the detection zone.

Preferably, the detection zone is a zone past which spermatozoa cannot flow (a 'trapping zone'). During operation, flow of spermatozoa is thus prevented beyond the trapping zone, and sperm are immobilized for detection. Preferably, the trapping zone utilizes principles disclosed in W000/20866—the zone is porous with a pore size such that spermatozoa cannot enter. During flow into the trapping zone, therefore, sperm are captured at an entrance; as sperm concentration increases, an amount retained there also increases.

The trapping zone can be made from any suitable porous material (e.g. HDPR, nitrocellulose) through which spermatozoa cannot migrate. This requirement is reflected in the pore size of the trapping zone. The head of a human spermatozoon is typically 3–5 μm in diameter, and tail length is approximately 50–60 μm. The pore size should be selected accordingly (e.g. nitrocellulose. with a nominal pore size between 5–8 μm), and an appropriate pore size may be determined empirically by simple experimentation.

It will be apparent that any porous material encountered before the trapping zone must, in contrast to the trapping zone, have a pore size large enough to allow spermatozoa to move relatively freely.

As is well known to those in the art, a nominal pore size of a porous material can be determined by hard particle challenge testing i.e. by determining a maximum diameter of spherical particles which can pass through the material. Alternatively, the pore size of a material may be determined by measuring its 'bubble point'. The bubble point is pressure required to force air through a (water) wet membrane, and correlates with the pore size as measured by particle retention (although at extremes of pressure and pore size, this correlation may be weaker). The bubble point is generally easier to measure than particle retention and is thus a preferred test when assessing pore size.

The entrance to the trapping zone is preferably narrow, such that sperm are focused to give a sharper signal.

As a less-preferred detection zone, immobilized anti-sperm antibody may be utilized.

In one embodiment of the detection zone, detection is based on acrosin. The detection zone will contain a reagent for detecting acrosin (e.g. see Mortimer, *Practical Laboratory Andrology* (1994), page 90) and the reagent zone will include a reagent such as proteinase K or the calcium ionophore A23187 [Perry et al. (1997) *J. Exp. Zool.* 279: 284–290; Perry et al. (1997) *J. Exp. Zool.* 279:291–300 (1997): Perry et al. (1996) *Human Reprod.* 11:1055–1062; Perry et al. (1995) *Fertil. Steril.* 64:150–159] which causes acrosomes to open. A preferred reagent for lysing acrosomes is a lysis buffer comprising 2% SDS, 100 µg/ml proteinase K in 10 mM Tris-HCl and 0.1 M EDTA. During migration, therefore, acrosin is released from the sperm and is detected downstream at the detection zone.

More usually, the reagent zone will contain a reagent which binds to intact spermatozoa or to one or more of components thereof, and this binding reaction is used to generate a visual signal. Preferably, therefore, the reagent zone is a 'labelling zone', containing a label capable of binding to spermatozoa. This is preferably used in conjunction with a trapping zone.

The label within the labelling zone can be any suitable reagent that can bind to spermatozoa, preferably giving a visible signal. Because only motile spermatozoa will reach the outlet port, the label need not be specific for sperm.

The label is typically an antibody which can bind to spermatozoa and which has been suitably tagged. It is preferred to use a visible tag, such as colloidal gold (which is visible as a pink color), although fluorescent, luminescent or radioactive tags can also he used. It will be appreciated that the term 'antibody' may include polyclonal and monoclonal antibodies, as well as antibody fragments (eg. $F(ab)_2$. Fc and the like), provided that anti-sperm reactivity is retained.

Preferred labels recognize a surface antigen which is present on a majority of a population of spermatozoa, rather than a subset. Whilst any sperm antigen may be used (e.g. P34H (W097/40836), SP-10 (W095/29188), see also EP-A-0387873), 'universal' antigens such as CD59 may also used. As an alternative, a stain, such as eosin, may be used.

It is preferred that the label is not activated (e.g. re-hydration of dehydrated label) until sample separation medium leaves the vessel. This can he achieved by arranging the labelling zone such that label therein is not activated until the first actuator has been operated. Label therefore remains static until motile spermatozoa have left the sample and entered the sample separation medium.

The labelling zone may be arranged in any suitable position such that its label can contact spermatozoa in the detection zone (e.g. sperm retained at the trapping zone). It may be upstream or downstream of the application zone, or may be integral therewith. If it is upstream, sample separation medium leaving the vessel should be able to contact the labelling zone separately from its contact with the application zone, in order to activate the label; if it is downstream or integral, flow will automatically activate the label.

Where the detection means includes both a 'trapping zone' and a 'labelling zone', the pore size of the trapping zone will be such that free label (not bound to spermatozoa) can flow therethrough, whereas label which is bound to spermatozoa cannot. During flow into the trapping zone, therefore, bound label is captured at the entrance. As sperm concentration increases, an amount of capture label also increases. It will be apparent that the label must be smaller than spermatozoa, such that free label is not retarded by the trapping zone.

Where the detection means utilizes a label, it preferably includes a zone downstream of the detection zone which retains unbound label (the 'label control' zone). This will typically comprise immobilized antibody which can bind to unbound label (e.g. if the label is a marine monoclonal antibody, the label control zone may utilize anti-mouse antibody). Label which passes through the detection zone (e.g. which is not captured on entry to the trapping zone) is thus retained within the label control zone, where it can be measured. A comparison of the amount of label in the detection zone and the label control zone allows semi-quantitative measurement of the amount of spermatozoa in the sample.

The application zone is where the sample separation medium leaving the vessel comes into contact with the spermatozoa detection means. It can he formed from any material suitable for allowing capillary flow of spermatozoa therethrough e.g. fibrous material, such as a pad of HDPE material, bonded polyester fiber, glass fiber, or the like.

It has been found, however, that spermatozoa tend to be retained within fibrous materials, thus reducing sensitivity. It is therefore preferred to use a non-fibrous application zone. Suitable examples include capillary tubes, space between two or more sheets of material juxtaposed in close proximity such that capillary flow can occur therebetween, or a series of parallel capillary channels or grooves. In such arrangements, if the labelling zone and the application zone are integral, this is preferably formed from more than one piece of material such that label can be applied during assembly. Where juxtaposed sheets are used, for instance, label can be applied to one or more sheets, and these can then be brought into proximity to permit capillary flow. Similarly, where parallel channels or grooves are used the label can be applied to this channelled material and, optionally, covered by a further sheet.

In a similar arrangement, capillary flow takes place past a fibrous material rather than through it. Whilst flowing past, liquid can enter the fibrous material (e.g. to re-hydrate a label impregnated therein), but the main capillary flow through the application zone of sperm is not within the fibrous material.

The application zone and the sample outlet port may be essentially unitary.

In preferred embodiments, flow of a sample to the detection zone is assisted by a downstream wick, to aid capillary movement.

During use of preferred devices, therefore, a migration path of motile sperm in the sample is: entry to the separation medium via the vessel's inlet port, exit from the separation medium via the vessel's outlet port (upon operation of the actuator after an incubation period), entry to the application zone, and capillary flow to the trapping zone, in which further migration is prevented. A visible signal at the trapping zone indicates presence of motile spermatozoa in the sample The visible signal provided by the detection means is preferably external to the vessel, and more preferably one which is also visible from an exterior of the device.

The detection means is preferably in the form of a lateral flow test strip mounted on the outside of the vessel.

It will be appreciated that the vessel may include more than one sample outlet port, each of which may lead to separate detection means. This allows independent tests on the same sample e.g. an assay for motile sperm on one strip and an assay for acrosome reaction on another strip. This can also be achieved by using a single outlet port that leads downstream to several separate detection means.

To enhance separation of motile and non-motile spermatozoa (e.g. EP-A-0437508), it is preferred that the device should be operated at an essentially fixed temperature. This will typically be between 30° C. and 44° C., preferably between 35° C. and 39° C., and more preferably fixed at or around 37° C. Preferably, therefore, the device includes a temperature sensor.

The temperature sensor may give a simple signal to indicate when an operating temperature has been reached. The device could be held in a user's hand, or inserted in a heated water bath, until the signal is given.

More preferably, however, the device also includes its own heat source, which can preferably be regulated e.g. using thermostatic control. The heat source should supply heat primarily to a region of the vessel which contains the sample separation medium. Power and control circuitry for the heat source may conveniently be concealed within an actuator button, or within a body of the device.

It will be appreciated that inclusion of temperature regulation in the device can operate independently from the device's other features.

The device of the invention may be used with any suitable liquid sample, which is preferably a semen sample. The device may include a receptacle for the sample. Preferably, this is in the form of a cup or sloping surface onto which a sample can be deposited, after which it collects at a base (e.g. in a well). The sample inlet can then be placed into contact with this collected sample. The receptacle may also include an overflow near its base. The receptacle may be integral with the device, or may be provided as a separate component to which the device may be attached before, during or after sample deposition and/or collection.

Advantageously, an interface between the receptacle and the vessel's inlet port (e.g. where the vessel attaches to the well) is of a defined area, thereby aiding assay reproducibility.

The device of the invention can be produced simply and cheaply. Furthermore, it can be used very easily, for instance by a home user. The invention thus provides an assay device which can be used at home as a basic screen of, for instance, male fertility.

The invention also provides corresponding processes. Thus, the invention provides a process for separating motile spermatozoa from a liquid sample, the process comprising steps of:
(a) providing a vessel having a sample inlet port, a closed sample outlet port, and a sample separation medium;
(b) allowing spermatozoa in a sample to migrate into the sample separation medium over a period of between 5 and 60 minutes (preferably around 30 minutes); and
(c) allowing the sample separation medium to leave the vessel by opening the sample outlet port.

The process may initially comprise a step of opening the inlet port.

Preferably, the process also comprises steps for detecting spermatozoa in the medium once it has exited the vessel. Thus the invention provides a process for separating and detecting motile spermatozoa in a liquid sample, comprising further steps of:
(i) allowing sample separation medium that leaves the outlet port to flow by capillary action into material capable of immobilizing spermatozoa;
(ii) contacting spermatozoa with a label; and
(iii) detecting label that is retained at an entrance to the material.

The invention further provides a process for separating and/or detecting spermatozoa, wherein sperm flow by capillary action takes place through non-fibrous material.

The invention further provides a process for separating motile and non-motile spermatozoa, wherein the process takes place at an essentially fixed temperature, preferably around 37° C.

BRIEF DESCRIPTION OF THE DRAWINGS

FIG. 2 shows this device after insertion into a receptacle.
FIGS. 3 to 6 show operation of this device.
FIGS. 7A–7F show an overview of using this device.
FIG. 8 shows a second device according to the invention, prior to operation.
FIG. 9 shows the device of FIG. 8 separated into its two constituent pieces.
FIG. 10 shows an exploded view of a top one of the two constituent pieces shown in FIG. 9.
FIGS. 11A–11B show a construction of a test strip assembly used in the device of FIG. 8.

DETAILED DESCRIPTION OF THE PREFERRED EMBODIMENTS

Figure 1:
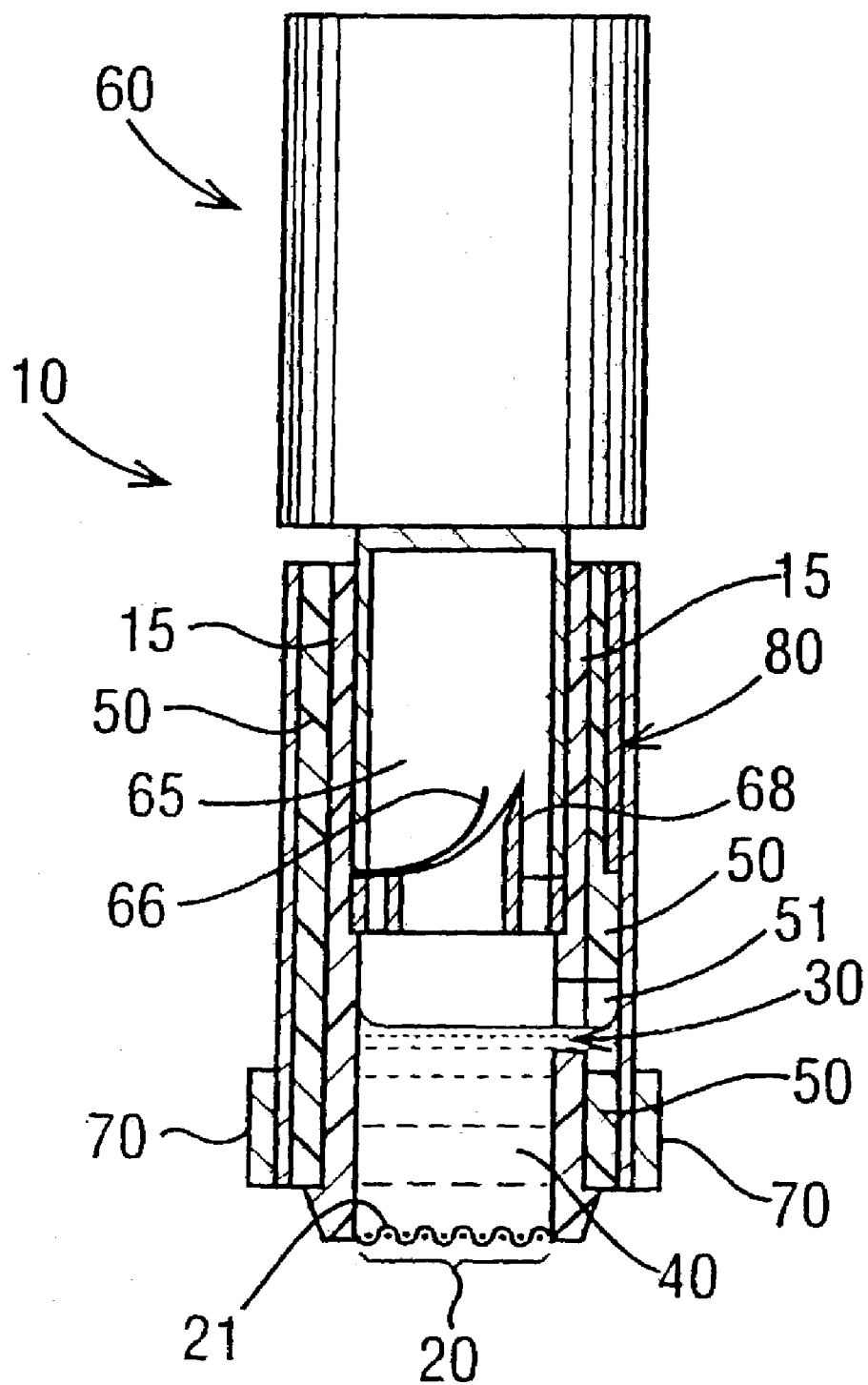
FIG. 1 shows a device according to the invention.

A device (10) shown in FIG. 1 comprises: a cylindrical plastic vessel (15); a sample inlet port (20), covered by a nylon mesh (21) formed from 0.15 mm strands spaced by 0.25 mm: a hole (30) in a side of the plastic vessel, shown in an open position: a solution (40) of EBSS supplemented with 0.88 mg/ml hyaluronic acid and 0.45% BSA; a plastic rotatable collar (50), including a hole (51) which is shown aligned with hole (30) to form an outlet port (35); a button (60, shown depressed), which houses a battery and circuitry for powering a circumferential heat source (70) and attached to which is a solution reservoir (65, shown empty), a foil seal (66, shown broken), and a hollow foil cutter (68); and an externally mounted test strip (80).

FIG. 2 shows the device (10) attached to a semen receptacle (90) with sloped walls. A semen sample (100) has collected in a well (99) at a base of the receptacle (90), but some of it has overflowed into a receptacle overflow (95).

FIG. 3 shows the device (10) immediately prior to use. A semen sample (100) has collected in the well (99) and is in contact with the inlet port (20). The outlet port (35) is closed because the hole (51) in the collar (50) is not aligned with the hole (30) in a wall of vessel 30. Solution (40) is held in reservoir (65) by foil seal (66), away from the inlet port (20).

Figure 4B:
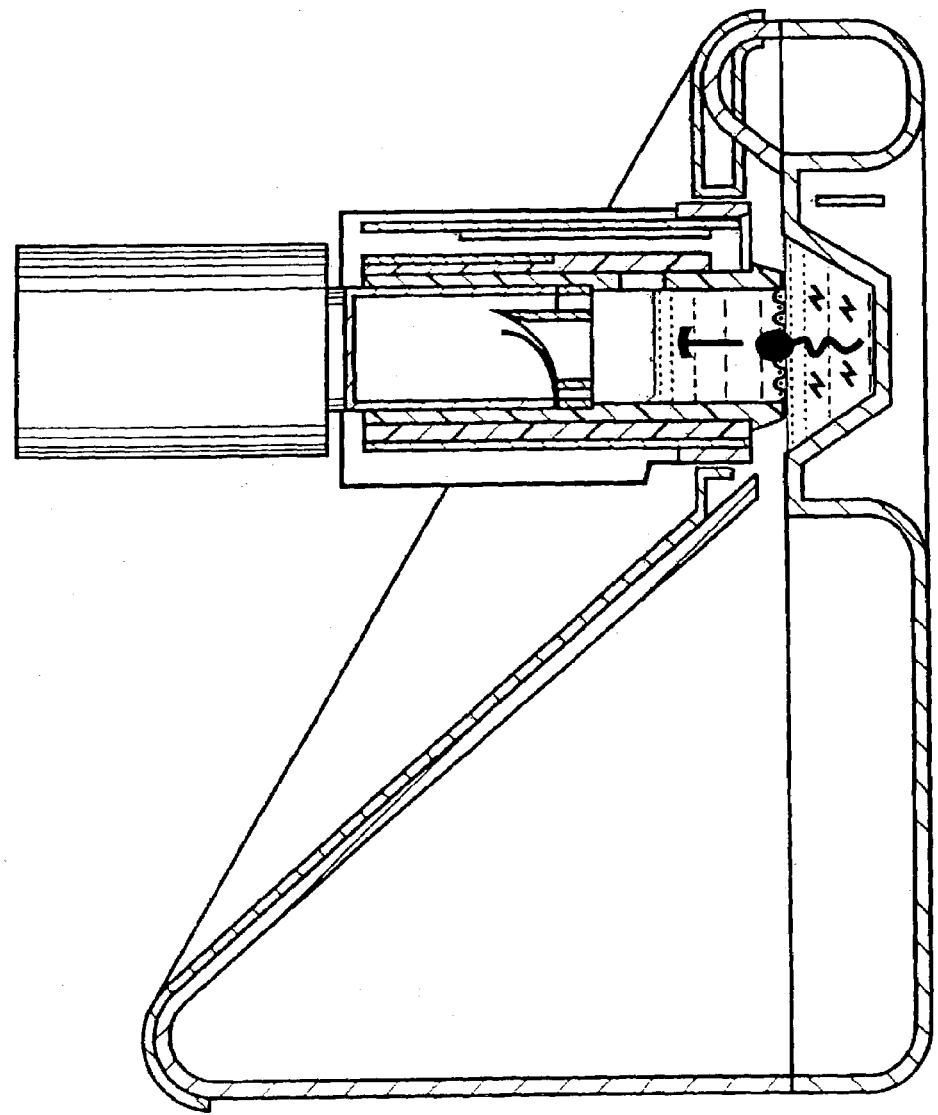

To initiate a test, button (60) is depressed, as shown in FIG. 4A. Foil cutter (68) pierces seal (66), releasing solution (40). Motile sperm in the sample (100) are now in liquid communication with solution (40) and are able to migrate into it through the inlet (20), as shown in FIG. 4B, whereas non-motile sperm and seminal plasma remain in sample (100). Button (60) also activates heat source (70), bringing a temperature of solution (40) to 37° C.

After a period of about 30 minutes, during which motile sperm have migrated into the solution (40), collar (50) is rotated, as shown in FIG. 5, so that its hole (51) aligns with hole (30), thereby opening the outlet port (35). Solution (40), now containing motile sperm, is free to leave the vessel and contact externally-mounted test strip (80).

As shown in FIG. 6, the solution flows by capillary action through closely-juxtaposed plastic strips (81a & 81b) at the base of the test strip (80). Between the strips (81a & 81b) is an area (82) of dehydrated gold-labelled murine anti-CD59. As the solution passes area (82) between the strips (81a & 81b), an antibody is re-hydrated and is able to bind to spermatozoa in the solution. Further downstream, the solution reaches nitrocellulose strip (83). A pore size of the strip (83) is too small to allow the spermatozoa to enter, so they are captured at its entrance (84). Free label continues to flow until it is captured downstream at a line (85) of immobilized anti-mouse antibody.

Figure 7A:
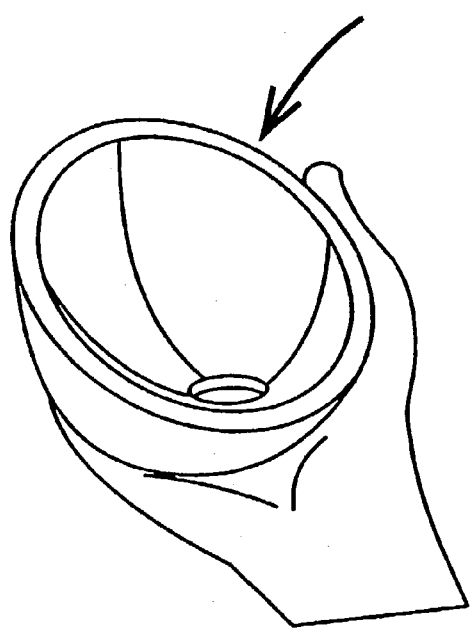
Figure 7B:
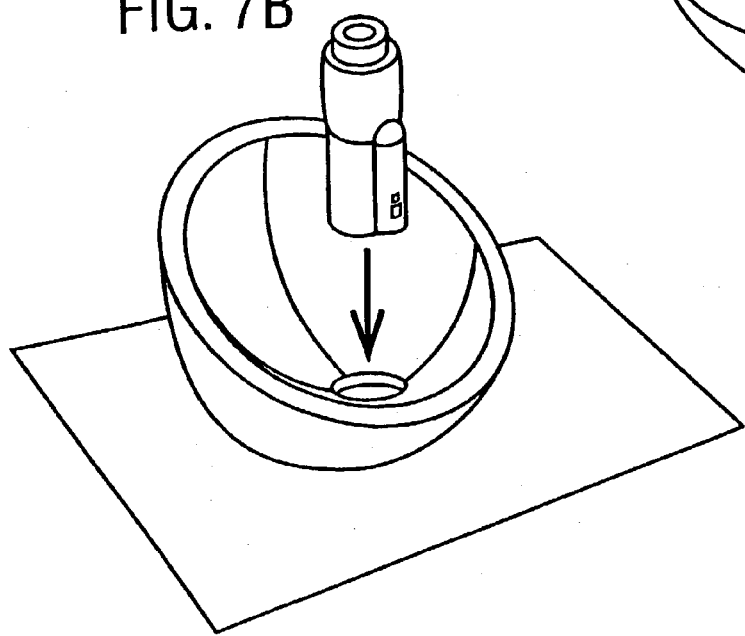
Figure 7C:
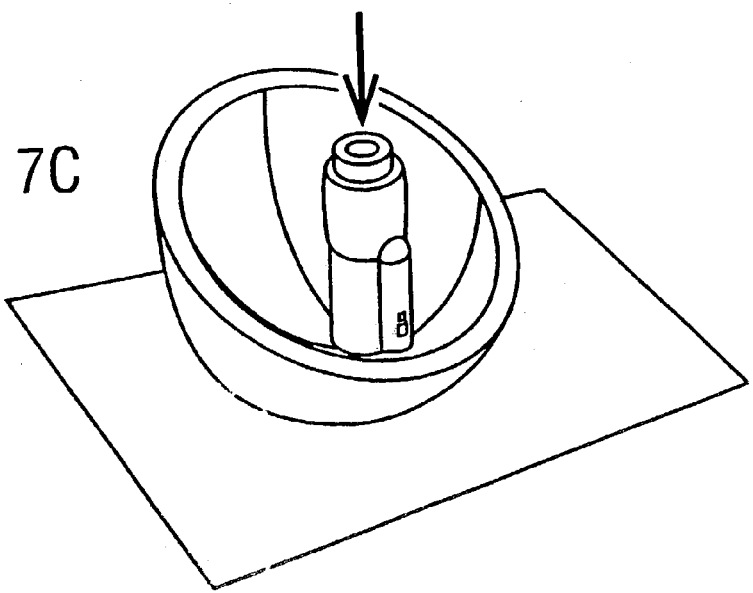

As shown in FIGS. 7A–7F, entrance (84) and line (85) are visible through windows. In FIG. 7E, two lines are visible, indicating presence of motile spermatozoa in an original sample. In contrast, only the control line (85) is visible in FIG. 7F, indicating an absence of motile sperm in the original sample.

Device (110) shown in FIGS. 8 and 9 comprises an upper piece (191) and a lower piece (190) which fit together. A base of lower piece (190) contains a well (199) into which a semen sample (200) is deposited. Upper piece (191) includes a recessed window (113), a button (160) and a rotatable knob (150). Knob (150) and button (160) are shaped such that knob (150) cannot be rotated until button (160) has been depressed.

In FIG. 10, internal components of upper piece (191) are shown in an exploded view. Upper piece (191) is formed from a top piece (192) which engages a seating (193). On a bottom of button (160) is a needle (168) and, when button (160) is operated, needle (168) pierces reservoir (165) which, prior to operation, contains a solution (140) of EBSS supplemented with 0.88 mg/ml hyaluronic acid and 0.45% BSA. Reservoir (165) sits in plastic housing (166), which has a neck portion (115) and a head portion (120). A side of neck portion (115) contains a hole (130) which engages a tube portion (186) of test strip assembly (180). A base of head portion (120) is covered by a circular nylon mesh (121) formed from 0.15 mm strands spaced by 0.25 mm. In assembled device (110), mesh (121) is in contact with sample (200) within well (199). Knob (150) is attached via a rack and pinion mechanism to plunger (155) which, prior to use, passes through tube (186) and towards hole (130). Seating (193) contains a battery (194) which powers heat source (170). When assembled, heat source (170) surrounds neck (115) circumferentially, except in the region of hole (130).

Exploded and assembled views of test strip assembly (180) are shown in FIGS. 11A and 11B. In the assembled device (110), tubular portion (186) communicates directly with hole (130) and, prior to use, plunger (155) engages and fills tube (186), thereby preventing liquid flow therethrough. As plunger (155) is withdrawn by operation of knob (150) in a direction of the arrow in FIG. 11, tube (186) opens to form, together with hole (130), an outlet port (135) through which liquid can flow. Tube (186) and plunger (155) therefore operate in the manner of a syringe. Liquid flows through tube (186) into a capillary space between clear plastic housings (181a: 181b) and passes under a pad (182) containing dehydrated gold-tagged murine anti-CD59. As liquid passes pad (182), an antibody is re-hydrated and can pass into the liquid, where it is able to bind to spermatozoa. The liquid continues to flow towards and into nitrocellulose strip (183), aided by a wick (188). A pore size of strip (183) is too small to allow the spermatozoa to enter, so they are captured at its entrance (184). Antibody can bind captured spermatozoa at entrance (184) and form a pink line. Any free antibody continues to flow until it is captured downstream at a line (185) of immobilised anti-mouse antibody.

Figure 12:
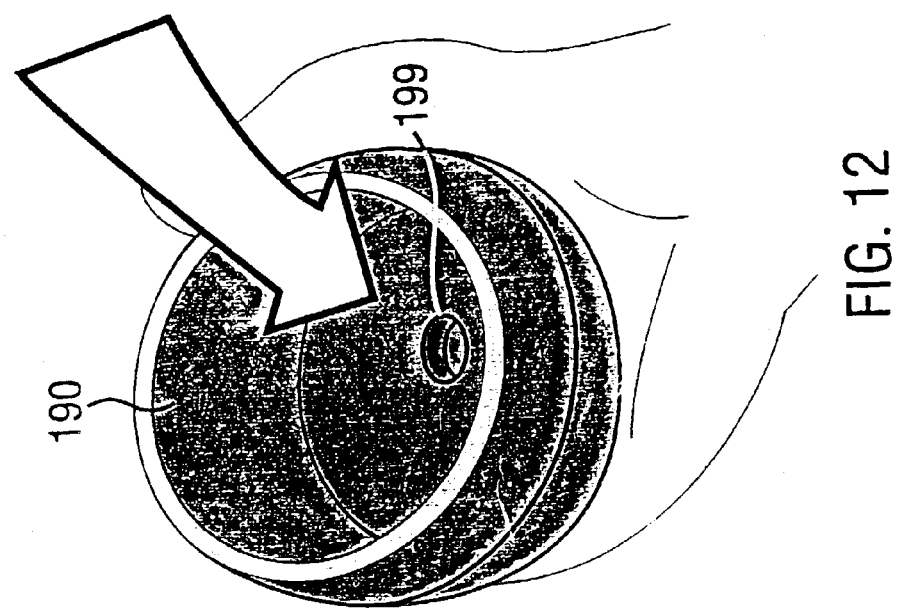

The device is used as illustrated in FIGS. 12 to 16:

In FIG. 12, a semen sample (200; e.g. obtained by masturbation) is placed into lower piece (190) and collects in well (199) whilst lower piece (190) rests on a flat surface.

Figure 13:
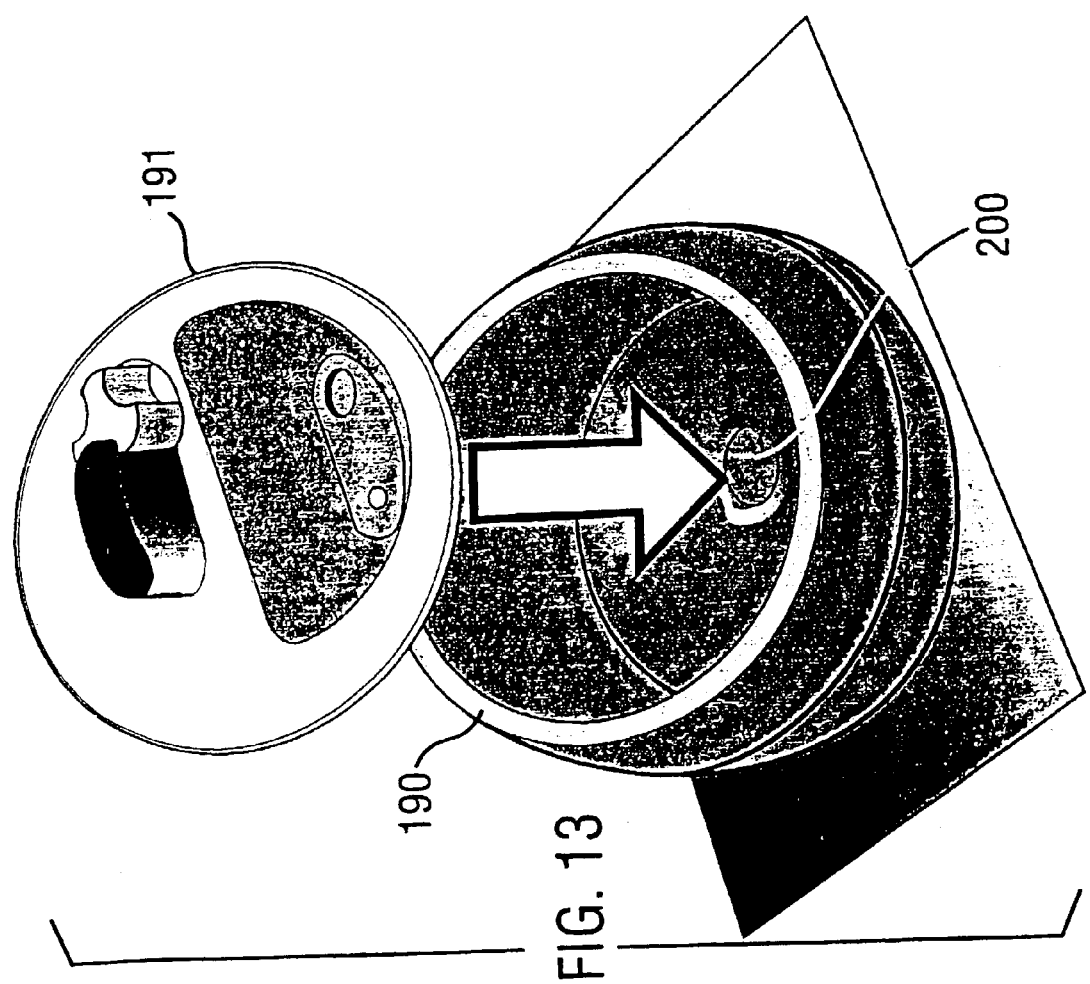
FIGS. 12 to 16 show an overview of using the device of FIG. 8.

After 30 minutes, upper piece (191) is assembled with lower piece (190) as shown in FIG. 13, to form device (110).

Figure 14:
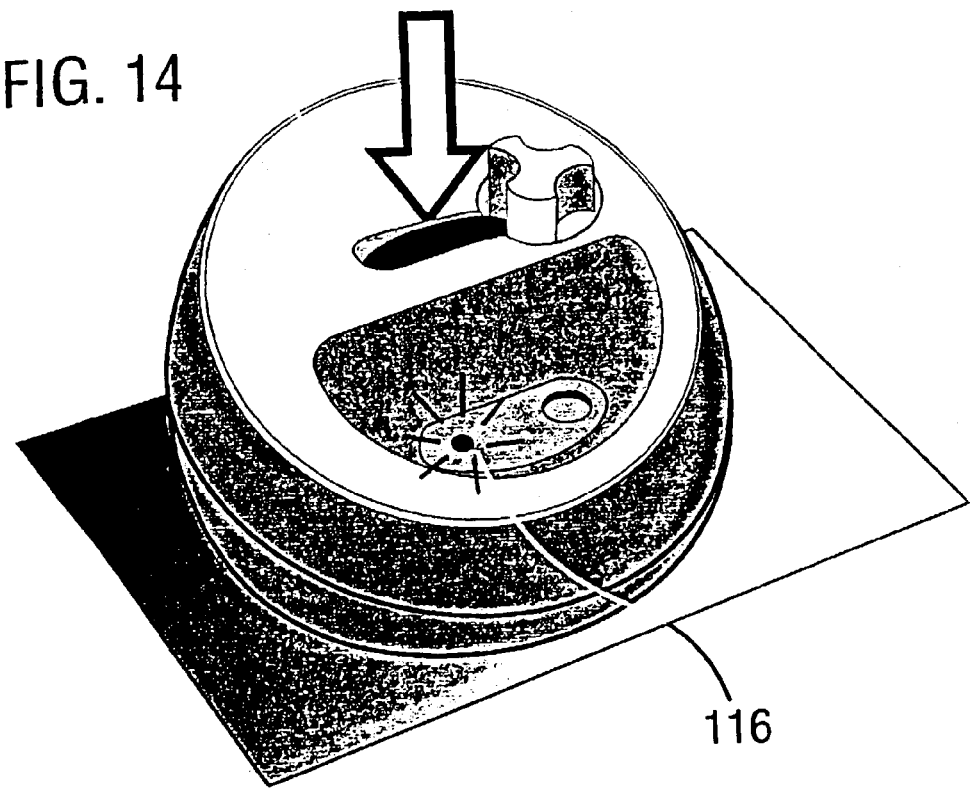

Button (160) is then depressed, as shown in FIG. 14. This releases solution (140) and also activates heat source (170), thereby bringing a temperature of solution (140) to 37° C.

Figure 15:
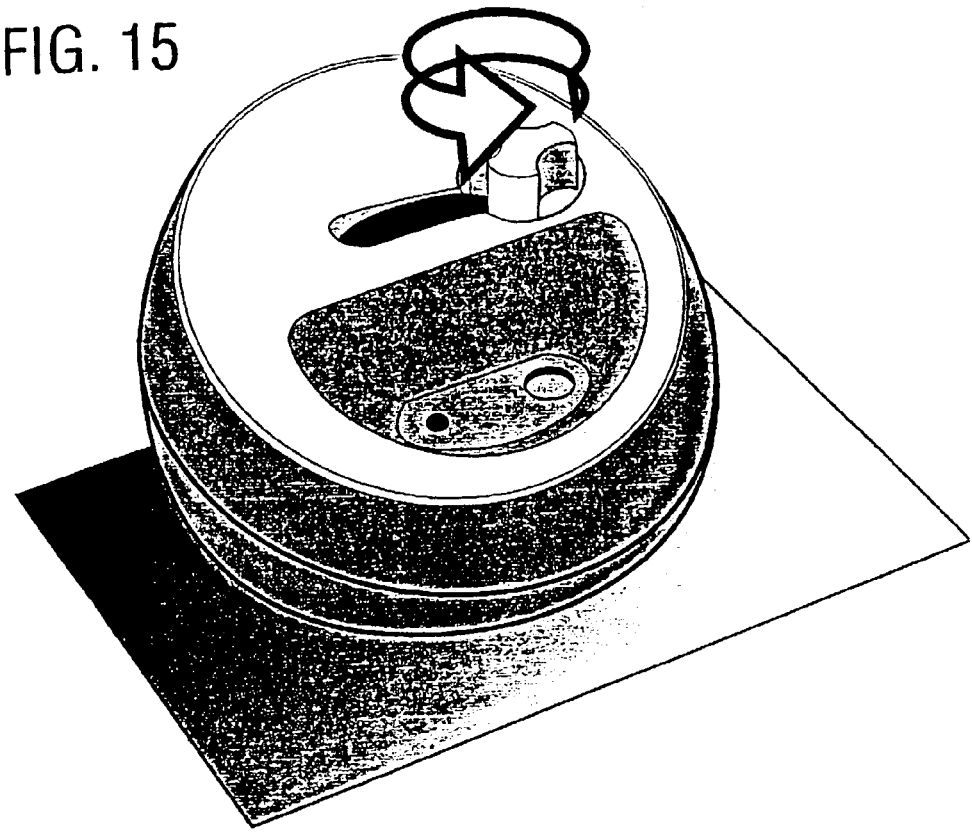
Figure 16:
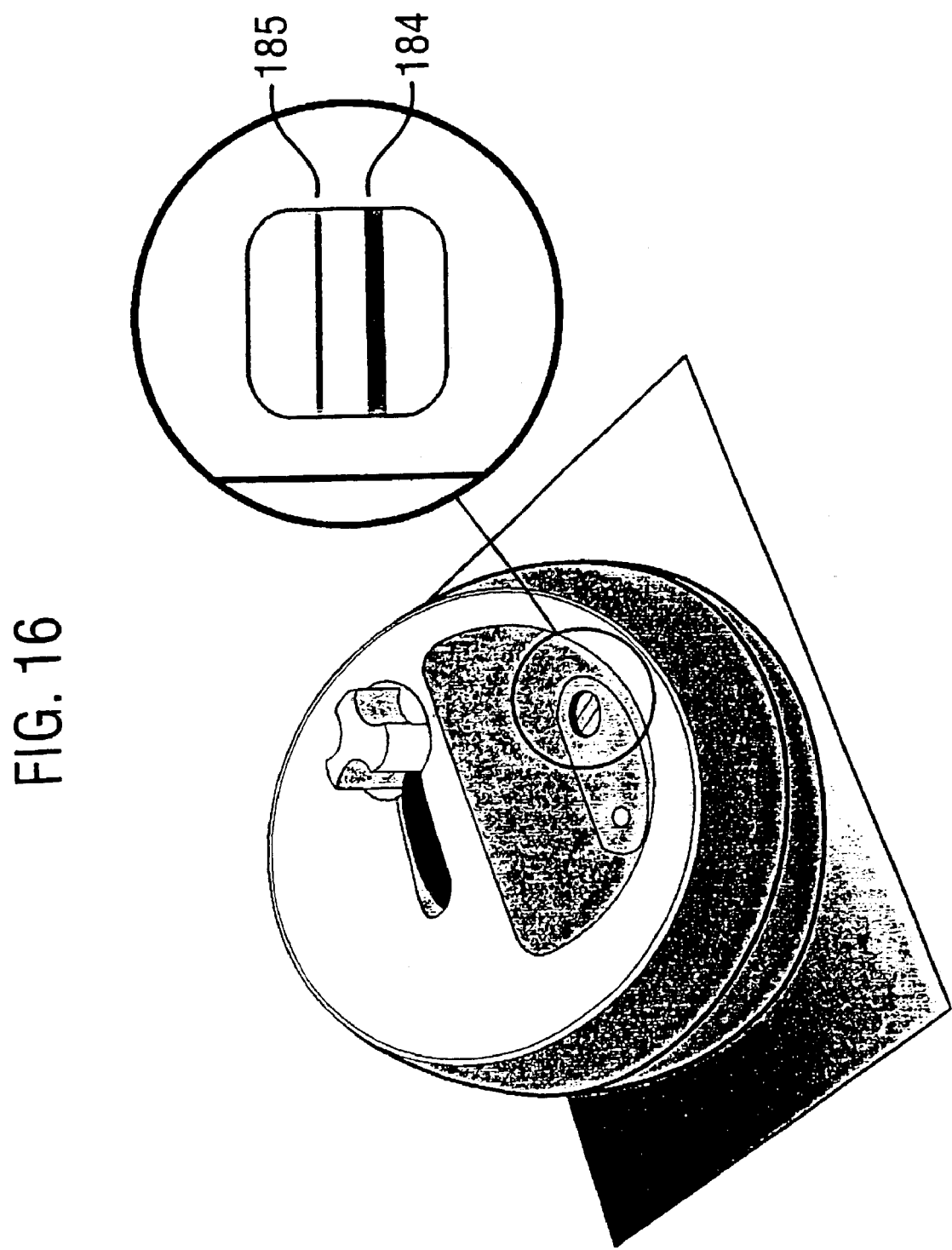

After around 30 minutes, to allow entry of sperm into solution (140) and also temperature equilibration, LED (116) indicates that knob (150) should be rotated, as in FIG. 15.

This withdraws plunger (135) and allows motile sperm from sample (200) which have swum into medium (140) to pass into the tube portion (186) of test strip (180). The solution (140) flows through the test strip (180) by capillary action towards wick (188). Sperm in the solution are retained at the entrance (184) of nitrocellulose strip (183). Free gold-tagged antibody continues to flow until it is captured downstream at a line (185) of immobilized anti-mouse antibody. The line at (184) in FIG. 16 indicates a positive result. The line at (185) indicates that the test has operated correctly.

It will be understood that the invention has been described by way of example only and modifications may be made whilst remaining within the scope and spirit of the invention.

The invention claimed is:

1. An apparatus for separating and detecting motile spermatozoa in a liquid sample, comprising:
   a separation vessel including
   (i) an inlet port,
   (ii) an outlet port arranged to be opened,
   (iii) a separation medium into which motile spermatozoa in the sample can flow via said inlet port, and
   (iv) an actuator operable to open said outlet port for allowing said separation medium to flow out of said vessel through said outlet port; and
   a spermatozoa detection device including
   (i) an application zone in communication with said outlet port,
   (ii) a detection zone, in which presence of spermatozoa can be detected, and
   (iii) a reagent zone containing a reagent which is capable of reacting with spermatozoa to facilitate detection of the spermatozoa in said detection zone, with said application zone, said detection zone and said reagent zone being arranged to permit capillary flow of spermatozoa from said application zone to said detection zone.

2. The apparatus according to claim 1, wherein
said application zone, said detection zone and said reagent zone are arranged to permit the capillary flow of the spermatozoa from said application zone to said detection zone via said reagent zone.

3. The apparatus according to claim 2, wherein
said detection zone comprises a spermatozoa-trapping zone capable of immobilizing spermatozoa, and
said reagent zone is a labeling zone containing label capable of binding to spermatozoa.

4. The device according to claim 2, wherein
said separation vessel further includes another actuator operable to allow said separation medium to come into communication with the sample via said inlet port.

5. The apparatus according to claim 2, wherein
said application zone is non-fibrous.

6. The apparatus according to claim 2, further comprising:
a temperature sensor.

7. The apparatus according to claim 1, wherein
said detection zone comprises a spermatozoa-trapping zone capable of immobilizing spermatozoa, and
said reagent zone is a labeling zone containing label capable of binding to spermatozoa.

8. The apparatus according to claim 7, wherein
said spermatozoa-trapping zone is porous with a pore size such that free label can flow therethrough, but label which is bound to spermatozoa cannot.

9. The apparatus according to claim 8, wherein
said detection device further includes a zone downstream of said detection zone for retaining label that is not bound to spermatozoa.

10. The apparatus according to claim 8, wherein
said application zone is non-fibrous.

11. The apparatus according to claim 8, further comprising:
a temperature sensor.

12. The apparatus according to claim 7, wherein
said detection device further includes a zone downstream of said detection zone for retaining label that is not bound to the spermatozoa.

13. The apparatus according to claim 12, wherein
said application zone is non-fibrous.

14. The apparatus according to claim 12, further comprising:
a temperature sensor.

15. The device according to claim 7, wherein
said separation vessel further includes another actuator operable to allow said separation medium to come into communication with the sample via said inlet port.

16. The apparatus according to claim 7, wherein
said application zone is non-fibrous.

17. The apparatus according to claim 7, further comprising:
a temperature sensor.

18. The apparatus according to claim 1, wherein
said separation vessel further includes another actuator operable to allow said separation medium to come into communication with the sample via said inlet port.

19. The device of claim 18, wherein
said detection zone is porous with a pore size such that free label can flow therethrough, but label which is bound to spermatozoa cannot.

20. The apparatus according to claim 18, wherein
said detection device further includes a zone downstream of said detection zone for retaining label that is not bound to spermatozoa.

21. The apparatus according to claim 18, wherein
said application zone is non-fibrous.

22. The apparatus according to claim 18, further comprising:
a temperature sensor.

23. The apparatus according to claim 1, wherein
said application zone is non-fibrous.

24. The apparatus according to claim 23, further comprising:
a temperature sensor.

25. The apparatus according to claim 1, further comprising:
a temperature sensor.

26. The apparatus according to claim 25, further comprising:
a heat source.

27. The apparatus according to claim 26, further comprising:
a temperature regulation device.

28. An apparatus for separating and detecting motile spermatozoa in a liquid sample, comprising:
a separation vessel including
  (i) an inlet port,
  (ii) an outlet port arranged to be opened,
  (iii) a separation medium into which motile spermatozoa in the sample can flow via said inlet port, and
  (iv) an actuator operable to open said outlet port for allowing said separation medium to flow out of said vessel through said outlet port; and
a spermatozoa detection device including
  (i) an application zone in communication with said outlet port,
  (ii) a trapping zone capable of immobilizing spermatozoa, and
  (iii) a labeling zone containing label capable of binding to spermatozoa,
  with said application zone, said trapping zone and said labeling zone being arranged to permit capillary flow of the spermatozoa from said application zone to said trapping zone.

* * * * *